United States Patent
Olsen

[11] Patent Number: 5,840,073
[45] Date of Patent: Nov. 24, 1998

[54] FILTER ARRANGEMENT FOR A COLLECTION BAG FOR BODY EXUDATES

[75] Inventor: Hans Olsen, Hørsholm, Denmark

[73] Assignee: Coloplast A/S, Espergaerde, Denmark

[21] Appl. No.: 809,252

[22] PCT Filed: Sep. 28, 1995

[86] PCT No.: PCT/DK95/00387

§ 371 Date: Mar. 20, 1997

§ 102(e) Date: Mar. 20, 1997

[87] PCT Pub. No.: WO96/10378

PCT Pub. Date: Apr. 11, 1996

[30] Foreign Application Priority Data

Sep. 30, 1994 [DK] Denmark ................... 1135/94

[51] Int. Cl.⁶ ....................................... A61F 5/44
[52] U.S. Cl. ........................................ 604/333
[58] Field of Search ...................... 604/332, 333

[56] References Cited

U.S. PATENT DOCUMENTS

| 4,211,224 | 7/1980 | Kubach et al. | 128/283 |
|---|---|---|---|
| 4,411,659 | 10/1983 | Jensen et al. | 604/332 |
| 4,451,258 | 5/1984 | Jenson | 604/333 |
| 4,512,771 | 4/1985 | Norton | 604/333 |
| 4,516,974 | 5/1985 | Davis | 604/333 |
| 4,940,461 | 7/1990 | Steer | 604/333 |
| 4,986,824 | 1/1991 | Steer et al. | 604/333 |
| 5,626,569 | 5/1997 | Holtermann et al. | 604/333 |

FOREIGN PATENT DOCUMENTS 2177301  1/1987  United Kingdom .

*Primary Examiner*—Robert A. Clarke
*Attorney, Agent, or Firm*—Ostrolenk, Faber, Gerb & Soffen, LLP

[57] ABSTRACT

A filter arrangement for a bag (1), in particular an ostomy bag with a vent (5), comprising a filter holder (7) fastened to the wall of the bag at the vent and having a through hole forming a passage from the interior of the bag to the surroundings, and a replaceable filter insert (8) designed for positioning in said hole. For position fixing of the filter insert in a use position, the filter holder has both means (13) for engagement with corresponding means (14) on the filter insert where the engagement means are designed such that upon positioning in the use position, the filter insert is prevented from being withdrawn from the filter holder, and within said engagement means has an elastically resilient clamping member (15) which in use position forms a sealing around the filter insert, but allows that this is pushed from the outside through the hole of the filter holder into the bag. The engagement means may be formed as an inwardly facing shoulder portion (13) in the filter holder (7) and a corresponding outwardly facing shoulder portion (14) on the filter insert (8). The filter insert has within said shoulder portion an internal conical end part with inwardly convergent cross section, and the elastically resilient clamping member (15) of the holder forms a sealing lip around said end part of the insert.

18 Claims, 1 Drawing Sheet

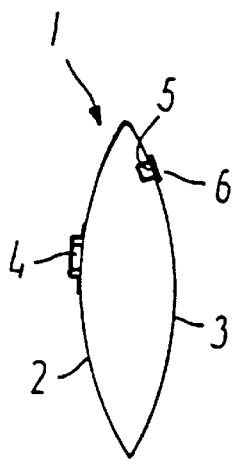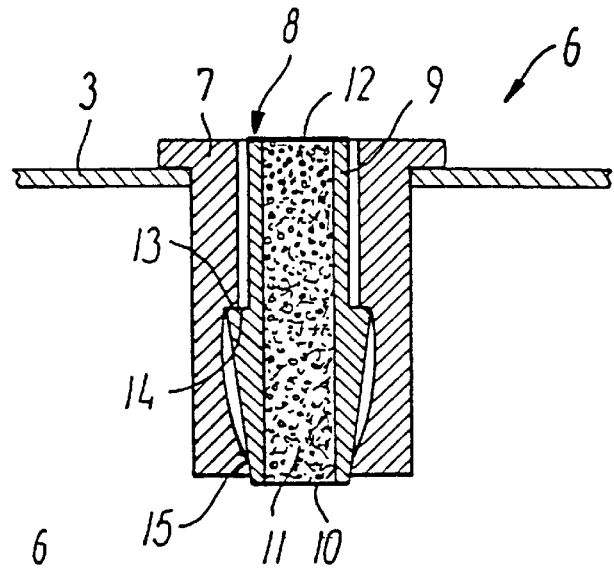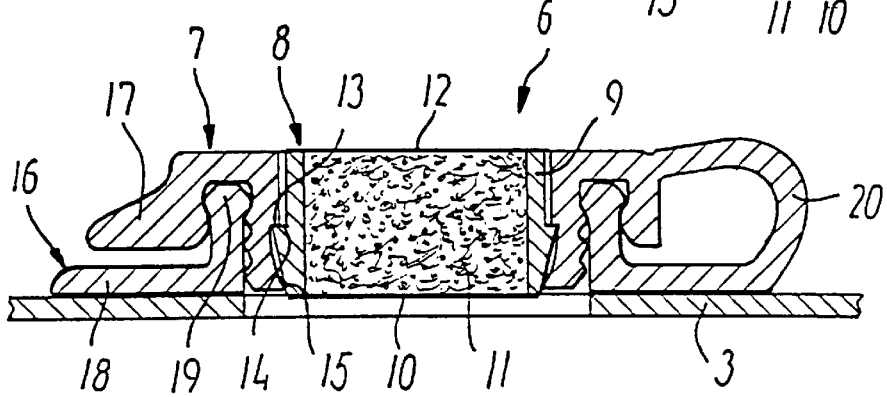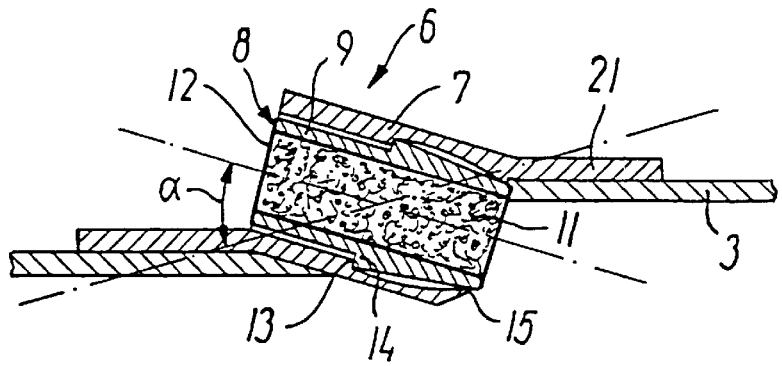
FIG. 1
FIG. 2
FIG. 3
FIG. 4

FILTER ARRANGEMENT FOR A COLLECTION BAG FOR BODY EXUDATES

BACKGROUND OF THE INVENTION

The invention relates to a filter arrangement for a collection bag for body exudates, in particular an ostomy bag with a vent, comprising a filter holder fastened to a wall of the bag at the vent and having a through hole forming a passage from the interior of the bag to the surroundings, and a replaceable filter insert designed for positioning in said hole.

DESCRIPTION OF THE PRIOR ART

It is known to design bags for collection or drainage with a vent for decharging gases which are accumulated in the bag during use and which without this precaution would entail a distension of the bag making the bag noticeable under the user's clothing. Especially in cases with ostomates who have been provided with an artificial opening formed surgically in the abdominal wall for connection of the intestinal system with the ostomy bag, the vent is usually equipped with some kind of deodorizing filter in order to avoid odor nuisances when the escaping flatus reaches the surroundings.

Furthermore, it is known to change the filter when it has lost its deodorizing effect or has been clogged such that the bag need not be disposed of due to the shorter life of the filter.

In prior art filter arrangements of the above-mentioned type as known eg. from DK publication no. 162 136, U.S. Pat. No. 4,411,659 and U.S. Pat. No. 4,451,258 a replaceable filter element is arranged in a filter holder. In these designs, the vent is open during the replacement thus permitting the flatus to escape, perhaps together with material collected in the bag if the user is eg. in a lying position. Besides, it will during replacement be necessary to touch the used filter element which must furthermore be disposed of, and the replacement must therefore be carried out in a place where the user may both discard the filter element and subsequently wash his or her hands.

SUMMARY OF THE INVENTION

With this end in view, it is an object of the invention to provide a filter arrangement which makes it easier and more comfortable for the user to replace the filter insert, the user avoiding touching the filter, and where during the replacement, the vent remains closed all the time and at the same time, a good retention of the filter insert is secured when the filter arrangement is in use.

This purpose is fulfilled by a filter arrangement which is characterized in that for position fixing of the filter insert in a use position, the filter holder has means for engagement with corresponding means on the filter insert which engagement means are designed such that upon positioning in the use position, the filter insert is prevented from being withdrawn from the filter holder, and that at the end of the filter holder facing the interior of the bag an elastically resilient clamping member is provided which in the use position forms a sealing around the filter insert but allows this to be pushed from the outside through the hole of the filter holder into the bag.

Thereby is provided a tight and secure fastening of the filter insert in the filter holder and, at the same time, no gases escape during replacement and furthermore, it is possible to place a new insert in the holder without touching the used, perhaps soiled, filter insert. Besides, there is obtained the advantage that the used filter insert is disposed of in connection with emptying the bag.

In a structurally simple embodiment, said engagement means are formed by an inwardly facing shoulder portion in the filter holder and a corresponding outwardly facing shoulder portion on the filter insert, where the filter insert within said shoulder portion has an internal conical end part with inwardly convergent cross section, and where the elastically resilient clamping member of the holder forms a sealing lip around said end part of the insert. By the complementary shape of the engagement means in the filter holder and on the filter insert, respectively, a seal and form locking connection between these components is obtained in the use position, at the same time as it is possible with one grip to replace the filter insert.

In a preferred embodiment of the invention, the filter holder is designed with two parts with a first annular socket part fastened to the bag wall whereas the through hole for the filter insert is formed in a second part designed as an openable plug part for placement in said socket part. By this embodiment, a ventilating possibility is provided when the filter is clogged and it is not possible and suitable to replace the filter insert. The plug part is in that case lifted from the socket part and the stale air in the bag is released whereafter the plug part is placed again on the socket part.

The plug part and the socket part of the filter holder may preferably be connected through an integrated hinge (film hinge) or an integrated strap by which it can be avoided that the plug part is mislaid or lost.

The socket forms appropriately an outwardly facing collar with relatively low height around the bag opening, whereas the plug part is formed essentially as a ring with a mainly U-shaped cross section for clamping engagement with the outwardly facing collar of the socket. This limits the height of the filter arrangement, the bag with the filter arrangement thus providing the discretion desired.

As a further advantage, a hose coupling for a hand shower hose may be placed on the socket of the holder thus providing a possibility for rinsing the bag.

The first annular socket part or filter holder may eg. be produced by moulding in a manner known per se. The filter insert may eg. be produced by moulding of a tube, after which the very filter is inserted, or perhaps by moulding direct around the filter. Alternatively, the filter insert may be extruded around the very filter whereupon the filter insert is embossed by an embossing tool in order to, on the exterior, form members for retaining the filter insert in the holder part.

A watertight, but gas-permeable membrane may be clued against the part of the filter insert facing the interior of the bag. A top covering for closure of the outward facing end of the filter holder may likewise be fastened by gluing in a manner known per se. The Filter arrangement may be fastened by gluing or welding to the front wall of the bag.

The invention will in the following be explained more in detail with reference to the schematical drawing, where

BRIEF DESCRIPTION OF THE DRAWING

FIG. 1 shows a filter arrangement according to the invention placed on an ostomy bag, FIG. 2 on a larger scale a sectional view of the filter arrangement according to the invention, FIG. 3 a view as in FIG. 2, but with another embodiment of the filter arrangement, and FIG. 4 a view as in FIG. 2, but with yet another embodiment of the filter arrangement.

DETAILED DESCRIPTION OF THE INVENTION

In FIG. 1 is shown a bag 1 which is meant for collection of body exudates and which in the shown embodiment is an ostomy bag consisting of two walls 2, 3. In the rear wall 2 of the bag which in the use position is the wall facing the user, there is an opening 4 which via non-illustrated fastening members known per se is meant for connection with the patient's stoma. In the bottom part of the bag is a drainage device, not shown, which is closed when the bag is in use, for emptying the bag of its content. A vent in the form of a hole 5 is designed in one of the walls 2, 3 of the bag or in a seam where the two walls are welded together. The vent 5 is meant for receiving a filter arrangement 6.

The structure of the filter arrangement 6 appears from FIG. 2 where a tiller holder 7 which may be moulded of plastic material is fastened by eg. gluing or welding on the place where the vent 5 is designed and which in the shown embodiment is the front wall 3 of the bag. In the filter holder 7 is placed a filter insert 8 with essentially cylindrical cross-sectional form and consisting of a moulded tube 9 with a watertight, but gas-permeable membrane 10 in the end facing the interior of the bag. A filter material 11 of a type known per se, such as active coal, is placed in the tube 9 which is closed at the end by a gas-permeable top covering 12 with at least the same gas-permeability as the membrane 10.

The filter holder 7 has engagement means for fastening of the filter insert 8 in the form of an inwardly facing shoulder portion 13 preventing the filter insert 8 in moving outwards in the way that a corresponding outwardly facing shoulder portion 14 on the filter insert 8 abuts on the shoulder portion 13 of the filter holder 7. In the end of the filter holder 7 facing the interior of the bag is a resilient clamping part which is here designed as a sealing lip 15 in sealing abutment against a conical end portion of the filter insert 8. The diameter of the filter holder 7 is ajdusted such that the tube 9 at an outer end edge has a diameter which essentially corresponds to the diameter of the inner end edge. During replacement of the filter insert, the used insert 8 placed in the filter holder 7 is pressed inwards in the way that a new filter insert is lead from the outside into the holder where the inner end edge of the new insert is pressed against the outer end edge of the filter insert 8 in the filter holder 7. The conical end portion eases this insertion and presses the sealing lip 15 radially outwards such that the used filter insert 8 falls down in the bag.

In FIG. 3 is shown another embodiment of the filter arrangement 6 having a first annular socket part 16 and a second openable plug part 17. The socket part 16 is by a flange portion 18 fastened to the bag wall 3 and has an outwardly facing collar 19 meant for engagement with the plug part 17. The plug part 17 has the form of a ring with U-formed cross-section for clamping engagement with the collar 19 on the socket part 16. The hole of the filter holder for receiving the filter insert 8 is designed in the plug part 17 and is in the same way as in the embodiment shown in FIG. 2 designed with engagement members 13, 14 for retention of the filter insert 8 which is designed in a corresponding way as in the above described embodiment. The plug part 17 is in this embodiment connected with the socket part 16 by means of a hinge 20 which may be a film hinge of a type known per se or an elastic strap whose ends are fastened to the socket part 16 and the plug part 17, respectively. In order to rinse the bag, a hose coupling for a hand shower hose may coupled be on the collar 19 on the socket part 16 after the plug part 17 has been opened.

Finally, in FIG. 4 is shown an embodiment where the filter holder 7 is designed with a flange portion 21 which is fastened by glue to the bag wall 3 in such a way that the longitudinal axis of the through hole of the filter holder forms an angle α which may eg. be placed in an interval between 5° and 450° with the general plane of the flange portion 21. A plane through the end section of the flange portion 21, however, forms another angle with said longitudinal axis. By this design, the filter holder 7 projects with the filter insert 8 obliquely into the bag 1 and has thus a small extent in a direction at right angles to the plane of the bag.

What is claimed is:

1. The combination of a collection bag for body exudates having a wall which includes a vent and a filter arrangement received in said vent and comprising a filter holder secured to said wall of the bag at said vent, said filter holder having one end facing the interior of the bag and having a through-bore forming a passage from said one end to the exterior of the bag and a removable filter insert for replaceable arrangement in said bore, said insert having an inner end and engagement means to engage said filter holder in a use position, said filter holder having means for engagement with said engagement means on said filter insert for fixing said filter insert in a use position, the said filter holder engagement means including means for preventing the said filter insert from being withdrawn from said filter holder, and a elastically resilient clamping member at said one end of said filter holder and adapted to form a seal around said filter insert in said use position while allowing the insert to be pushed from the outside through the bore of said filter holder into the interior of the bag.

2. The combination according to claim 1, wherein said filter holder engagement means comprises an inwardly facing shoulder and the filter insert engagement means comprises a corresponding and outwardly facing shoulder which includes an internal conical end part with inwardly convergent cross-section, said clamping member forming a sealing lip around said end part.

3. The combination of claim 1, wherein said filter holder comprises a coherent molded component of plastic material.

4. The combination of claim 1, wherein said filter holder comprises two parts, said first part comprising a first annular socket part secured to said bag wall and said second part defining said through bore and comprising an openable plug for arrangement in said first annular socket part.

5. The combination of claim 4, wherein said plug and said socket part are connected by an integrated hinge.

6. The combination of claim 4, wherein said plug and said socket part are connected by an integrated strap.

7. The combination according to claim 4, wherein said socket part comprises an outwardly facing collar with a relatively low height around the bag opening and said plug comprises a ring with mainly U-shaped cross-section for clamping arrangement with said outwardly facing collar.

8. The combination according to claim 4, further comprising a hose coupling associated with said socket part.

9. The combination according to claim 1, wherein said filter holder comprises a flange portion adhered to the outer side of said wall.

10. The combination according to claim 9, wherein the longitudinal axis of said through-bore of said filter holder forms a relatively small acute angle with said flange portion.

11. The combination according to claim 1, wherein said insert comprises an essentially tubular molded component containing an active material therein.

12. The combination according to claim 11, wherein said inner end of said insert is closed by a water tight, gas-permeable membrane.

13. The combination of claim 1, wherein said collection bag is an ostomy bag.

14. The combination according to claim 13, wherein said insert comprises an essentially tubular molded component containing an active material therein and said inner end of said insert is closed by a water tight, gas-permeable membrane.

15. The combination according to claim 14, wherein said filter holder comprises a flange portion adhered to the outer side of said wall.

16. The combination of claim 15, wherein said filter holder comprises two parts, said first part comprising a first annular socket part secured to said bag wall and said second part defining said through bore and comprising an openable plug for arrangement in said first annular socket part.

17. The combination according to claim 16, wherein said filter holder engagement means comprises an inwardly facing shoulder and the filter insert engagement means comprises a correspondingly outwardly facing shoulder which includes an internal conical end part with inwardly conversion cross-section, said clamping member forming a sealing lip around said end part.

18. The combination according to claim 17, wherein said socket part comprises an outwardly facing collar with a relatively low height around the bag opening and said plug comprises a ring with mainly U-shaped cross-section for clamping arrangement with said outwardly facing collar.

* * * * *